(12) United States Patent
Heidenfelder et al.

(10) Patent No.: US 6,416,773 B2
(45) Date of Patent: Jul. 9, 2002

(54) COSMETIC OR DERMATOLOGICAL LIGHT PROTECTION AGENT PREPARATIONS

(75) Inventors: Thomas Heidenfelder, Römerberg (DE); Volker Schehlmann, Rockaway Township, NJ (US); Thomas Wünsch, Speyer; Wilma M. Dausch, Limburgerhof, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/771,593

(22) Filed: Jan. 30, 2001

(30) Foreign Application Priority Data

Feb. 29, 2000 (DE) .......................... 100 09 442
Sep. 7, 2000 (DE) .......................... 100 44 351

(51) Int. Cl.$^7$ .................... A61K 6/00; A61K 7/04; A61K 31/12; G03C 5/00
(52) U.S. Cl. .................. 424/401; 424/59; 430/269; 514/685
(58) Field of Search .................. 430/269; 424/401, 424/59; 514/685

(56) References Cited

U.S. PATENT DOCUMENTS

| 4,387,089 A | | 6/1983 | De Polo | 424/59 |
| 4,514,231 A | | 4/1985 | Kerner et al. | 106/309 |
| 5,510,228 A | * | 4/1996 | Neumann et al. | 430/269 |
| 5,576,354 A | | 11/1996 | Deflandre et al. | 514/685 |
| 5,587,150 A | | 12/1996 | Deflandre et al. | 424/59 |

FOREIGN PATENT DOCUMENTS

| DE | 33 14 742 | | 10/1984 |
| FR | 2 440 933 | | 6/1980 |
| WO | WO-93/15063 | * | 8/1993 |

OTHER PUBLICATIONS

Deflandre et al. "Photostability assessment of sunscreens. Benzylidene camphor and dibenzoylmethane derivatives" Intl. Journal of Cosmetic Science vol. 10 pp. 53–62 (1988).

* cited by examiner

Primary Examiner—Michael G. Hartley
Assistant Examiner—Michael A. Willis
(74) Attorney, Agent, or Firm—Keil & Weinkauf

(57) ABSTRACT

The invention relates to cosmetic or dermatological preparations comprising a) 0.1 to 10% by weight of one or more 3,3-diphenylacrylates of the formula I,

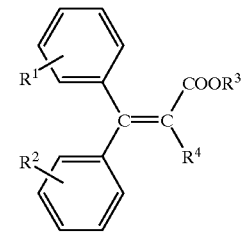

I and b) 0.1 to 10% by weight of one or more dibenzoylmethane derivatives of the formula II,

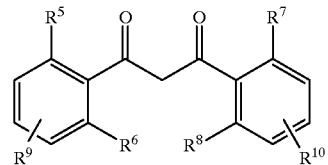

II in which the substituents $R^1$ to $R^{10}$ independently of one another have the meanings given in the description.

11 Claims, No Drawings

COSMETIC OR DERMATOLOGICAL LIGHT PROTECTION AGENT PREPARATIONS

The invention relates to cosmetic or dermatological light protection agent preparations comprising a combination of one or more 3,3-diphenylacrylates and one or more dibenzoylmethane derivatives, and to the use thereof for the protection of human skin or human hair against UV rays.

The light protection agents used in cosmetic and dermatological preparations have the task of preventing or at least diminishing the extent of the harmful effects of sunlight on the human skin. In addition, these light protection agents, however, also serve to protect other ingredients from decomposition or degradation by UV radiation. In hair cosmetic formulations, the aim is to prevent damage to the keratin fiber by UV rays.

The sunlight which reaches the earth's surface contains UV-B radiation (280 to 320 nm) and UV-A radiation (>320 nm), which directly border the visible light region. The effect on human skin is evident, particularly in the case of UV-B radiation, from sunburn.

The erythema activity maximum of sunlight is given as the relatively narrow region around 308 nm.

Numerous compounds are known for protecting against UV-B radiation; these are, inter alia, derivatives of 3-benzylidenecamphor, of 4-aminobenzoic acid, of cinnamic acid, of salicylic acid, of benzophenone, and of 2-phenylbenzimidazole.

For the region between about 320 nm and about 400 nm, the UV-A region, it is also important to have available filter substances, since the rays of that region can also trigger reactions in cases of skin which is sensitive to light. It has been found that UV-A radiation leads to damage of the elastic and collagenic fibers of connective tissue, which leads to premature aging of the skin, and that it is to be regarded as a cause of numerous phototoxic and photoallergic reactions. The harmful effect of UV-B radiation can be intensified by UV-A radiation.

To protect against UV-A rays, derivatives of dibenzoylmethane are used, although their photostability is inadequate (Int. J. Cosm. Science 10, 53 (1988)).

French Patent Specification 2,440,933 describes 4-(1,1-dimethylethyl)-4'-methoxydibenzoylmethane as UV-A filter. It is proposed to combine this particular UV-A filter, which is sold by GIVAUDAN under the name "PARSOL 1789", with different UV-B filters in order to absorb all the UV rays having a wavelength of from 280 to 380 nm.

However, this UV-A filter, when used alone or in combination with UV-B filters, is insufficiently photochemically stable to ensure lasting protection of the skin during a prolonged session of sunbathing, which requires repeated applications at regular and brief intervals if effective protection of the skin against all UV rays is desired.

For this reason, according to U.S. Pat. No. 5,587,150 and U.S. Pat. No. 5,576,354, the insufficiently photostable UV-A filters are stabilized by the addition of 2-cyano-3,3-diphenylacrylates, which themselves serve as filters in the UV-B region.

The combinations of dibenzoylmethane and 2-cyano-3,3-diphenylacrylate mentioned in U.S. Pat. No. 5,587,150 and U.S. Pat. No. 5,576,354 have the disadvantage that the preparations prepared therewith in many cases still have inadequate cosmetic properties, such as, for example, tackiness which is too high and, associated therewith, an unsatisfactory feel on the skin.

It is an object of the invention to provide novel stabilizers for UV-A filters from the class of dibenzoylmethanes which do not have the abovementioned disadvantages.

It is furthermore an object of the present invention to propose light protection agents for cosmetic and dermatological purposes which absorb in the UV-A region with high absorbance, which are photostable, have low intrinsic color, i.e. a sharp band structure, and are readily processable in oil or water.

We have found that this object is achieved by cosmetic or dermatological preparations comprising a) 0.1 to 10% by weight of one or more 3,3-diphenylacrylates of the formula I,

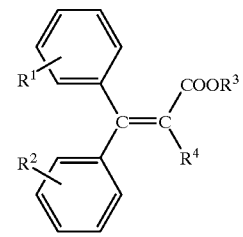

I in which the substituents independently of one another have the following meanings:

$R^1$ and $R^2$ are hydrogen, $C_1$–$C_{12}$-alkyl, $C_1$–$C_{12}$-alkoxy;

$R^3$ is $C_3$–$C_{10}$-cycloalkyl, optionally substituted;

$R^4$ is hydrogen, CN and b) 0.1 to 10% by weight of one or more dibenzoylmethane derivatives of the formula II,

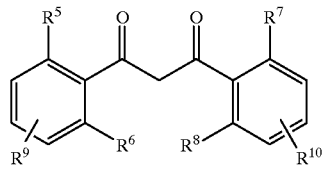

II in which the substituents independently of one another have the following meanings:

$R^5$ to $R^8$ are hydrogen, $C_1$–$C_4$-alkyl;

$R^9$ and $R^{10}$ are hydrogen, $C_1$–$C_{12}$-alkyl, $C_1$–$C_{12}$-alkoxy.

Alkyl radicals for $R^1$ and $R^2$ and also $R^9$ and $R^{10}$ which may be mentioned are branched or unbranched $C_1$–$C_{12}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, 2-ethylhexyl, 1,1,3-trimethylhexyl, 1,1,3,3-tetramethylpentyl, n-nonyl, n-decyl, n-undecyl, 1-methylundecyl, n-dodecyl.

Alkyl radicals for $R^5$ to $R^8$ which may be mentioned are branched or unbranched $C_1$–$C_4$-alkyl chains, preferably methyl, ethyl, n-propyl, 1-methylethyl, n-butyl, 1-methylpropyl, 2-methylpropyl, 1,1-dimethylethyl.

Suitable alkoxy radicals for $R^1$ and $R^2$ and also $R^9$ and $R^{10}$ are straight-chain and branched radicals having 1 to 12 carbon atoms, preferably having 1 to 8 carbon atoms.

Examples which may be mentioned are:
methoxy ethoxy
isopropoxy n-propoxy
1-methylpropoxy n-butoxy
n-pentoxy 2-methylpropoxy
3-methylbutoxy 1,1-dimethylpropoxy
2,2-dimethylpropoxy hexoxy
1-methyl-1-ethylpropoxy heptoxy
octoxy 2-ethylhexoxy Cycloalkyl radicals for $R^3$ which may be mentioned are $C_3$–$C_{10}$-cycloalkyl radicals, such as cyclopropyl, cyclobutyl, cyclopentyl, cyclohexyl, cycloheptyl, cyclooctyl. Preference is given to $C_5$–$C_8$-cycloalkyl, such as cyclopentyl, cyclohexyl, cycloheptyl and cyclooctyl, in particular cyclopentyl and cyclohexyl.

The cycloalkyl radicals can be optionally substituted by up to three radicals, including halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl or $C_1$–$C_4$-alkoxy, or contain 1 to 3 heteroatoms, such as sulfur, nitrogen whose free valencies may be saturated by hydrogen or $C_1$–$C_4$-alkyl, or oxygen.

The cycloalkyl radicals may also be present as bicyclic ring systems.

Preferred substituents on the cycloalkyl ring are $C_1$–$C_4$-alkyl groups, in particular methyl, ethyl, n-propyl, 1-methylethyl, n-butyl, 1-methylpropyl, 2-methylpropyl, 1,1-dimethylethyl.

Particularly preferred substituents for $R^3$ are the cycloalkyl radicals listed below.

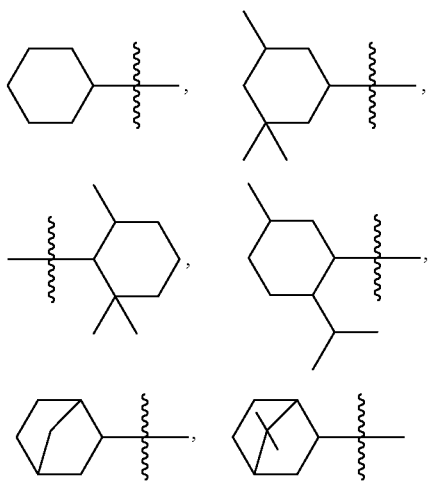

Preference is given to cosmetic or dermatological preparations comprising
a) 0.1 to 10% by weight of one or more 3,3-diphenylacrylates of the formula Ib,

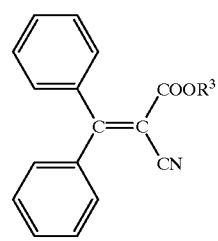

in which $R^3$ is $C_5$–$C_8$-cycloalkyl, optionally substituted and b) 0.1 to 10% by weight of one or more dibenzoylmethane derivatives, chosen from the group consisting of 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane.

Particular preference is given to cosmetic or dermatological preparations comprising
a) 0.1 to 10% by weight of one or more 3,3-diphenylacrylates of the formula Ib,

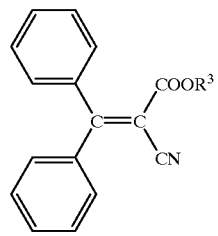

in which $R^3$ is $C_5$–$C_8$-cycloalkyl, optionally substituted and b) 0.1 to 10% by weight of 4-tert-butyl-4'-methoxydibenzoylmethane.

The content of component a) in the cosmetic or dermatological light protection agent preparations according to the invention is in the range from 0.1 to 10% by weight, preferably from 0.1 to 6% by weight, particularly preferably in the range from 0.3 to 3% by weight, very particularly preferably in the range from 1.5 to 2.5% by weight.

The content of component b) in the cosmetic or dermatological light protection agent preparations according to the invention is in the range from 0.1 to 10% by weight, preferably from 0.2 to 7% by weight, particularly preferably in the range from 0.3 to 6% by weight, very particularly preferably in the range from 0.4 to 5% by weight.

The molar ratio of components a) and b) in the cosmetic or dermatological preparations is in a range a:b of from 0.5 to 10, preferably in a range from 1 to 8.

The cosmetic or dermatological preparations according to the invention exhibit a sunscreen factor of greater than 5, preferably greater than 10, particularly preferably greater than 20, very particularly preferably greater than 25.

The cosmetic and dermatological preparations comprising light protection agents are generally based on a carrier which comprises at least one oil phase. Accordingly, oils, oil-in-water and water-in-oil emulsions, creams and pastes, lip protection stick compositions or grease-free gels are suitable.

Cosmetic and dermatological preparations according to the invention furthermore advantageously comprise inorganic pigments based on metal oxides and/or other metal compounds which are insoluble or virtually insoluble in water, in particular the oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and also mixtures of such oxides. Particular preference is given to pigments based on $TiO_2$.

For the purposes of the present invention, it is particularly advantageous, although not obligatory, for the inorganic pigments to be in hydrophobic form, i.e. for them to have been treated superficially to repel water. This surface treatment can involve providing the pigments with a thin hydrophobic layer by methods known per se.

Such a process involves, for example, producing the hydrophobic surface layer by a reaction in accordance with

$$nTiO_2 + m(RO)_3Si\text{—}R' \rightarrow nTiO_2 \quad \text{(surf.)}$$

here, n and m are stoichiometric parameters to be used as desired, and R and R' are the desired organic radicals. For example, hydrophobized pigments prepared analogously to DE-A 33 14 742 are advantageous.

Advantageous $TiO_2$ pigments are obtainable, for example, under the tradenames MT 100 T from TAYCA, and also M 160 from Kemira, and T 805 from Degussa.

The cosmetic or dermatological light protection preparations advantageously comprise inorganic pigments, in particular micropigments, in amounts of, for example, 0.1% by weight to 30% by weight, preferably in amounts from 0.5% by weight to 15% by weight, particularly preferably from 1% by weight to 10% by weight, very particularly preferably from 1.5 to 6% by weight, based on the total weight of the preparations.

The cosmetic and/or dermatological light protection formulations according to the invention can have the customary composition and be used for cosmetic and/or dermatological light protection, and also the treatment, care and cleansing of the skin and/or hair, and as make-up product in decorative cosmetics.

For use, the cosmetic and dermatological preparations according to the invention are applied to the skin and/or the hair in a sufficient amount in the manner customary for cosmetics.

Particular preference is given to cosmetic and dermatological preparations which are in the form of a sunscreen. These can advantageously additionally comprise at least one other UV-A filter and/or at least one further UV-B filter and/or at least one inorganic pigment, preferably an inorganic micropigment.

The cosmetic and dermatological preparations according to the invention can comprise cosmetic auxiliaries as are customarily used in such preparations, e.g. preservatives, bactericides, perfumes, antifoams, dyes, pigments which have a coloring action, thickeners, moisturizing and/or humectant substances, fats, oils, waxes or other customary constituents of a cosmetic or dermatological formulation, such as alcohols, polymers, foam stabilizers, electrolytes, organic solvents or silicone derivatives.

An additional content of antioxidants is generally preferred. According to the invention, favorable antioxidants are all antioxidants which are customary or suitable for cosmetic and/or dermatological applications.

The antioxidants are advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes (e.g. α-carotene, β-carotene, lycopene) and derivatives thereof, chlorogenic acid and derivatives thereof, liponic acid and derivatives thereof (e.g. dihydroliponic acid), aurothioglucose, propylthiouracil and other thiols (e.g. thioredoxin, glutathion, cysteine, cystine, cystamine and the glycosyl, N-acetyl, methyl, ethyl, propyl, amyl, butyl and lauryl, palmitoyl, oleyl-, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocystein sulfoximine, buthionine sulfones, penta-, hexa-, heptathionine sulfoximine) in very small tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, furfurylidenesorbitol and derivatives thereof, ubiquinone and ubiquitol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and koniferyl benzoate of benzoin, rutinic acid and derivatives thereof, α-glycosylrutin, ferulic acid, furfurylideneglucitol, carnosene, butylhydroxytoluene, butylhydroxyanisol, nordihydroguaiac acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

The amount of the abovementioned antioxidants (one or more compounds) in the preparations is preferably 0.001 to 30% by weight, particularly preferably 0.05 to 20% by weight, in particular 1 to 10% by weight, based on the total weight of the preparation.

If vitamin E and/or derivatives thereof are the antiodixant(s), it is advantageous to choose their respective concentrations from the range from 0.001 to 10% by weight, based on the total weight of the formulation. If vitamin A or vitamin A derivatives or carotenes or derivatives thereof are the antioxidant(s), it is advantageous to choose their respective concentrations from the range from 0.001 to 10% by weight, based on the total weight of the formulation.

The lipid phase can advantageously be chosen from the following groups of substance:

mineral oils, mineral waxes oils, such as triglycerides of capric or of caprylic acid, but preferably castor oil;

fats, waxes and other natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids; alkyl benzoates;

silicone oils, such as dimethylpolysiloxanes, diethylpolysiloxanes, diphenylpolysiloxanes and mixed forms thereof.

The oil phase of the emulsions, oleogels or hydrodispersions or lipodispersions for the purposes of the present invention is advantageously chosen from the group of esters of saturated and/or unsaturated, branched and/or unbranched alkanecarboxylic acids of chain length from 3 to 30 carbon atoms, from the group of esters of aromatic carboxylic acids and saturated and/or unsaturated, branched and/or unbranched alcohols of chain length from 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil.

The oil phase can furthermore advantageously be chosen from the group of branched and unbranched hydrocarbons and hydrocarbon waxes, silicone oils, dialkyl ethers, the group of saturated or unsaturated, branched or unbranched alcohols, and the fatty acid triglycerides, namely the triglycerol esters of saturated and/or unsaturated, branched and/or unbranched alkanecarboxylic acids of chain length from 8 to 24, in particular 12 to 18, carbon atoms. The fatty acid triglycerides can, for example, be advantageously chosen from the group of synthetic, semisynthetic and natural oils, e.g. olive oil, sunflower oil, soybean oil, groundnut oil, rapeseed oil, almond oil, palm oil, coconut oil, palm kernel oil and the like.

Also, any mixtures of such oil and wax components can be advantageously used for the purposes of the present invention. It may also be advantageous in some instances to use waxes, for example cetyl palmitate, as the sole lipid component of the oil phase.

The oil phase is advantageously chosen from the group consisting of 2-ethylhexyl isostearate, octyldodecanol, isotridecyl isononanoate, isoeicosane, 2-ethylhexyl cocoate, $C_{12-15}$-alkylbenzoate, caprylic/capric triglyceride, dicaprylic ether.

Particularly advantageous mixtures comprise $C_{12-15}$-alkyl benzoate, 2-ethylhexyl isostearate and isotridecyl isononanoate.

Of the hydrocarbons, paraffin oil, squalane and squalene are advantageous for the purposes of the present invention.

The oil phase can further advantageously have a content of cyclic or linear silicone oils or consist entirely of such oils, although it is preferred, apart from the silicone oil or silicone oils, to use an additional content of other oil phase components.

Cyclomethicone (octamethylcyclotetrasiloxane) is advantageously used as the silicone oil to be used according to the invention. However, other silicone oils are also advantageous for the purposes of the present invention, for example, hexamethylcyclotrisiloxane, polydimethylsiloxane, poly (methylphenylsiloxane).

Other particularly advantageous mixtures comprise cyclomethicone and isotridecyl isononanoate, or cyclomethicone and 2-ethylhexyl isostearate.

The aqueous phase of the preparations according to the invention optionally advantageously comprises alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and in particular one or more thickeners, which can advantageously be chosen from the group consisting of silicon dioxide, aluminum silicates, polysaccharides or derivatives thereof, e.g. hyaluronic acid, xanthan gum, hydroxypropylmethylcellulose, particularly advantageously from the group of polyacrylates, preferably a polyacrylate from the group of so-called Carbopols, for example Carbopols types 980, 981, 1382, 2984, 5984, each individually or in combination.

It is further advantageous, apart from the combinations according to the invention, to use additional oil-soluble organic UV-A filters and/or UV-B filters in the lipid phase and/or water-soluble organic UV-A filters and/or UV-B filters in the aqueous phase, the total amount of filter substances being, for example, 0.1% by weight to 30% by weight, preferably 0.5 to 15% by weight, in particular 1 to 10% by weight, based on the total weight of the preparations, in order to make available cosmetic preparations which protect the skin from the entire region of ultraviolet radiation.

Examples which may be mentioned are:

TABLE 1

| No. | Substance | CAS No. (=acid) |
|---|---|---|
| 1 | 4-aminobenzoic acid | 150-13-0 |
| 2 | 3-(4'-trimethylammonio)benzylidenebornan-2-one methylsulfate | 52793-97-2 |
| 3 | 3,3,5-trimethylcyclohexyl salicylate (homosalate) | 118-56-9 |
| 4 | 2-hydroxy-4-methoxybenzophenone (oxybenzone) | 131-57-7 |
| 5 | 2-phenylbenzimidazole-5-sulfonic acid and its potassium, sodium and triethanolamine salts | 27503-81-7 |
| 6 | 3,3'-(1,4-phenylenedimethine)bis(7,7-dimethyl-2-oxobicyclo[2.2.1]heptane-1-methanesulfonic acid) and its salts | 90457-82-2 |
| 7 | polyethoxyethyl 4-bis(polyethoxy)aminobenzoate | 113010-52-9 |
| 8 | 2-ethylhexyl 4-dimethylaminobenzoate | 21245-02-3 |
| 9 | 2-ethylhexyl salicylate | 118-60-5 |
| 10 | isoamyl 4-methoxycinnamate | 71617-10-2 |
| 11 | 2-ethylhexyl 4-methoxycinnamate | 5466-77-3 |
| 12 | 2-hydroxy-4-methoxybenzophenone-5-sulfonic acid (sulisobenzone) and the sodium salt | 4065-45-6 |
| 13 | 3-(4'-sulfobenzylidene)bornane-2-one and salts | 58030-58-6 |
| 14 | 3-benzylidenebornane-2-one | 16087-24-8 |
| 15 | 1-(4'-isopropylphenyl)-3-phenylpropane-1,3-dione | 63260-25-9 |
| 16 | 4-isopropylbenzyl salicylate | 94134-93-7 |
| 17 | 2,4,6-trianilino(o-carbo-2'-ethylhexyl-1'-oxy)-1,3,5-triazine | 88122-99-0 |
| 18 | 3-imidazol-4-ylacrylic acid and its ethyl ester | 104-98-3 |
| 19 | menthyl o-aminobenzoate or: 5-methyl-2-(1-methylethyl)-2-aminobenzoates | 134-09-8 |
| 20 | glyceryl p-aminobenzoate or: 1-glyceryl 4-aminobenzoate | 136-44-7 |
| 21 | 2,2'-dihydroxy-4-methoxybenzophenone (dioxybenzone) | 131-53-3 |
| 22 | 2-hydroxy-4-methoxy-4-methylbenzophenone (mexenone) | 1641-17-4 |
| 23 | triethanolamine salicylate | 2174-16-5 |
| 24 | dimethoxyphenylglyoxalic acid or: sodium 3,4-dimethoxyphenylglyoxalate | 4732-70-1 |
| 25 | 3-(4'-sulfobenzylidene)bornan-2-one and its salts | 56039-58-8 |
| 26 | 2,2',4,4'-tetrahydroxybenzophenone | 131-55-5 |
| 27 | 2,2'-methylenebis[6-(2H-benzotriazol-2-yl)-4-(1,1,3,3,-tetramethylbutyl)phenol] | 103597-45-1 |
| 28 | 2,2'-(1,4-phenylene)bis-1H-benzimidazole-4,6-disulfonic acid, Na salt | 180898-37-7 |
| 29 | 2,4-bis[4-(2-ethylhexyloxy)-2-hydroxy]phenyl-6-(4-methoxyphenyl)-(1,3,5)triazine | 187393-00-6 |
| 30 | 3-(4-methylbenzylidene)camphor | 36861-47-9 |
| 31 | polyethoxyethyl 4-bis(polyethoxy)paraaminobenzoate | 113010-52-9 |
| 32 | 2,4-dihydroxybenzophenone | 131-56-6 |
| 33 | 2,2'-dihydroxy-4,4'-dimethoxybenzophenone-5,5'-disodium sulfonate | 3121-60-6 |

Other light protection agents which can be combined are, inter alia, the following compounds:

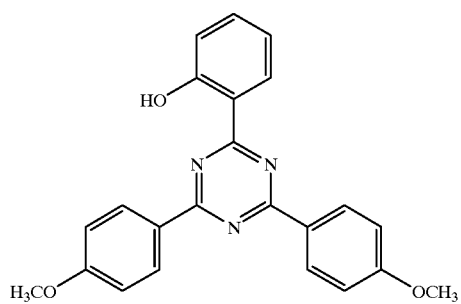
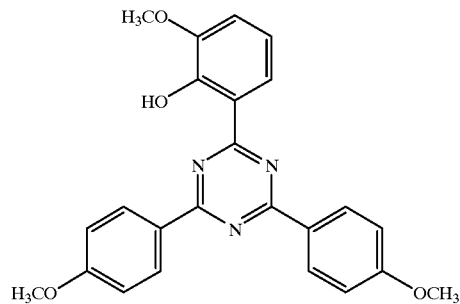
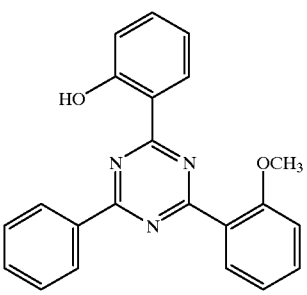
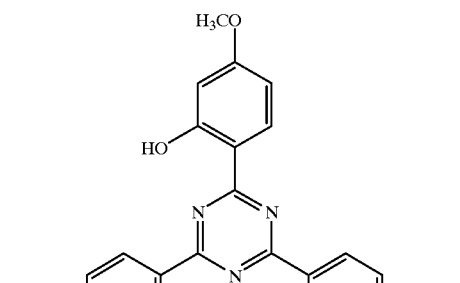
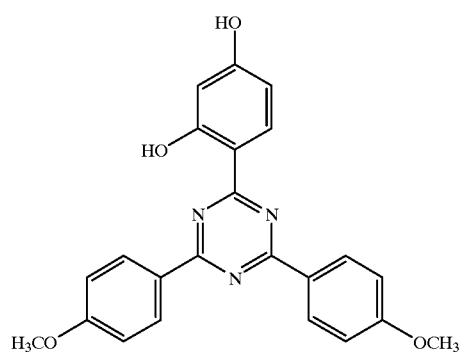
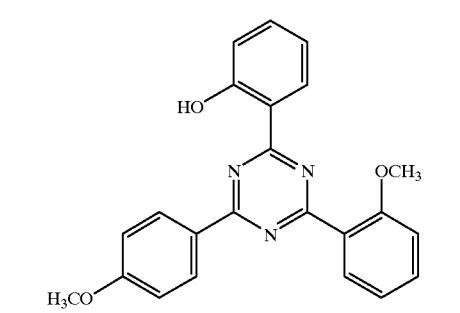

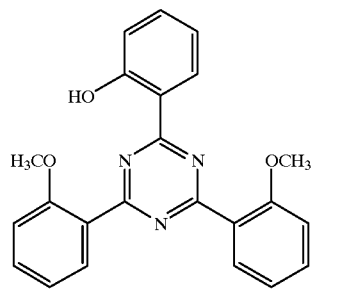
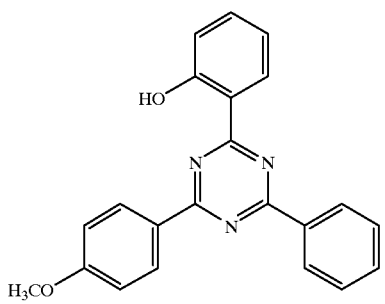
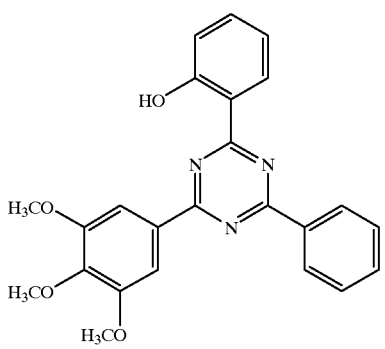
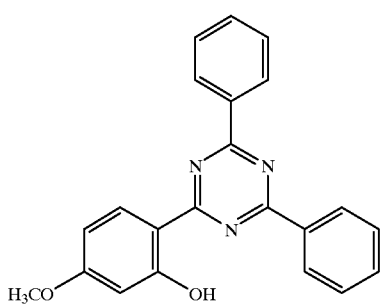
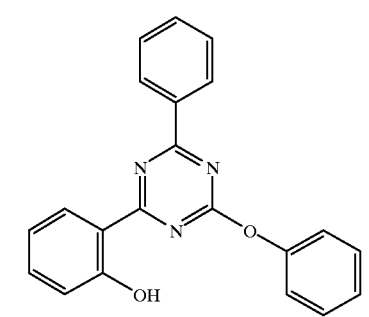
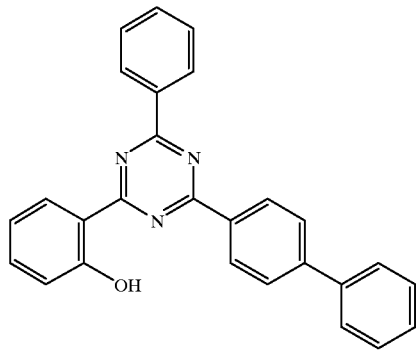
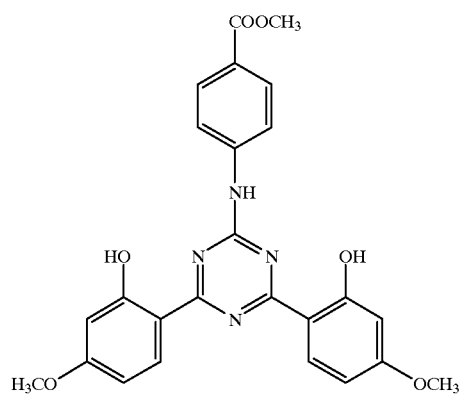

-continued

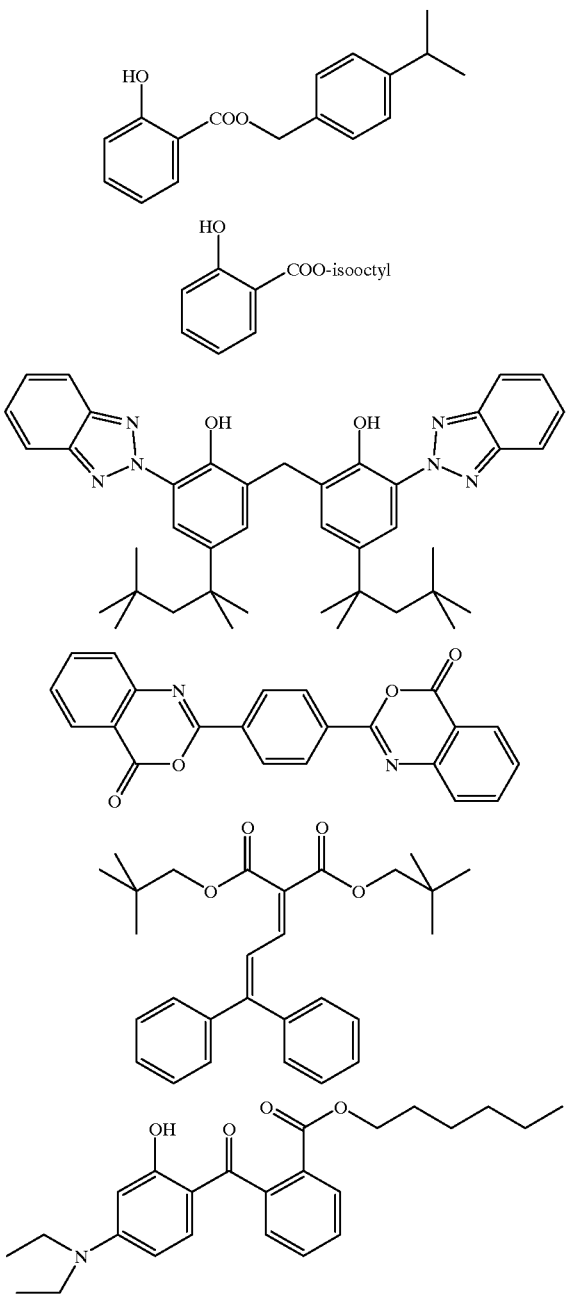

The list of UV filters given which can be used in combination with the active ingredient combinations according to the invention is not, of course, intended to be limiting.

To protect human hair against UV rays, the light protection preparations according to the invention can be used as shampoos, lotions, gels, hair sprays, aerosol foam creams or emulsions, inter alia, for washing, coloring and for styling the hair.

The UV filter action of the preparations according to the invention can also be utilized for stabilizing active ingredient and auxiliaries in cosmetic and dermatological formulations.

The combination according to the invention is particularly notable for the fact that it leads to significant photostabilization of dibenzoylmethane derivatives (see Example 14).

The examples below serve to illustrate the present invention without limiting it.

I. PREPARATION

EXAMPLE 1

Cyclopentyl 2-cyano-3,3-diphenylacrylate 83.1 g (0.3 mol) of ethyl 2-cyano-3,3-diphenylacrylate (Uvinul 3035), 100 ml of cyclopentanol and 6 g of $Na_2CO_3$ were reacted with one another at 145° C. with distillative removal of the ethanol formed, assisted by a stream of nitrogen. After about 3 h, the reaction mixture was filtered hot in order to remove the $Na_2CO_3$. After the filtrate had been cooled, the precipitate which had formed was filtered off, washed with petroleum ether and dried, giving 78.1 g (82%) of cyclopentyl 2-cyano-3,3-diphenylacrylate as a colorless solid. [$\lambda_{max}$ 300 nm; $E_1^1$ (MeOH) 395]

EXAMPLE 2

Cyclohexyl 2-cyano-3,3-diphenylacrylate 139 g (0.5 mol) of ethyl 2-cyano-3,3-diphenylacrylate (Uvinul 3035), 200 ml of cyclohexanol and 10 g of $Na_2CO_3$ were reacted together at 150° C. with distillative removal of the ethanol formed, assisted by a stream of nitrogen. After about 6 h, the reaction mixture was filtered hot in order to remove the $Na_2CO_3$. After the filtrate had been cooled, the precipitate which had formed was filtered off, washed with petroleum ether and dried, giving 111 g (67%) of cyclohexyl 2-cyano-3,3-diphenylacrylate as a colorless solid. [$\lambda_{max}$ 300 nm; $E_1^1$, (MeOH) 381]

EXAMPLE 3

4-tert-butylcyclohexyl 2-cyano-3,3-diphenylacrylate 139 g (0.5 mol) of ethyl 2-cyano-3,3-diphenylacrylate (Uvinul 3035), 200 ml of 4-tert-butylcyclohexanol and 10 g of $Na_2CO_3$ were reacted together at 182° C. with distillative removal of the ethanol formed, assisted by a stream of nitrogen. After about 4 h, the reaction mixture was diluted with 300 ml of methanol and filtered hot in order to remove the $Na_2CO_3$. After the filtrate had been cooled, the precipitate which had formed was filtered off, washed with petroleum ether and dried, giving 130 g (67%) of 4-tert-butylcyclohexyl 2-cyano-3,3-diphenylacrylate as a colorless solid. [$\lambda_{max}$ 302 nm; $E_1^1$ (MeOH) 324]

EXAMPLE 4

Norbornyl 2-cyano-3,3-diphenylacrylate 55.4 g (0.2 mol) of ethyl 2-cyano-3,3-diphenylacrylate (Uvinul 3035), 100 g of norborneol and 4 g of $Na_2CO_3$ were reacted with one another at about 185° C. with distillative removal of the ethanol formed, assisted by a stream of nitrogen. After about 4 h, the reaction mixture was filtered hot in order to remove the $Na_2CO_3$. After the filtrate had been cooled, the precipitate which had formed was filtered off, washed with cyclohexane and dried, giving 37 g (53%) of norbornyl 2-cyano-3,3-diphenylacrylate [$\lambda_{max}$=304 nm, $E_1^1$ =386] as a colorless solid.

EXAMPLE 5

2,2,6-Trimethylcyclohexyl 2-cyano-3,3-diphenylacrylate 55.4 g (0.2 mol) of ethyl 2-cyano-3,3-diphenylacrylate (Uvinul 3035), 100 ml of 2,2,6-trimethylcyclohexanol and 4 g of Na$_2$CO$_3$ were reacted with one another at 184–186° C. with distillative removal of the ethanol formed, assisted by a stream of nitrogen. After about 3 h, the reaction mixture was filtered hot in order to remove the Na$_2$CO$_3$. After the filtrate had been cooled, it was distilled under reduced pressure, giving 55 g (74%) of 2,2,6-trimethylcyclohexyl 2-cyano-3,3-diphenylacrylate [$\lambda_{max}$=304 nm, $E_1^1$=351] as a colorless solid.

EXAMPLE 6

3,3,5-Trimethylcyclohexyl 2-cyano-3,3-diphenylacrylate 55.4 g (0.2 mol) of ethyl 2-cyano-3,3-diphenylacrylate (Uvinul 3035), 100 ml of 3,3,5-trimethylcyclohexanol and 4 g of Na$_2$CO$_3$ were reacted with one another at 181–184° C. with distillative removal of the ethanol formed, assisted by a stream of nitrogen. After about 5 h, the reaction mixture was filtered hot in order to remove the Na$_2$CO$_3$. After the filtrate had been cooled, the precipitate which had formed was filtered off, washed with cyclohexane and dried, giving 29 g (39%) of 3,3,5-trimethylcyclohexyl 2-cyano-3,3-diphenylacrylate [$\lambda_{max}$=301 nm, $E_1^1$=344] as a colorless solid.

EXAMPLE 7

Menthyl 2-cyano-3,3-diphenylacrylate 55.4 g (0.2 mol) of ethyl 2-cyano-3,3-diphenylacrylate (Uvinul 3035), 62.5 g of menthol and 4 g of Na$_2$CO$_3$ were reacted with one another at 185–200° C. with distillative removal of the ethanol formed, assisted by a stream of nitrogen. After about 6 h, the reaction mixture was cooled and distilled under reduced pressure, giving 44 g (57%) of menthyl 2-cyano-3,3-diphenylacrylate [$\lambda_{max}$=300 nm, $E_1^1$=351].

II. PREPARATIONS

EXAMPLE 8

Composition for lip care

| Mass content (% by weight) | |
|---|---|
| ad 100 | Eucerinum anhydricum |
| 10.00 | glycerol |
| 10.00 | titanium dioxide, micronized |
| 3.00 | cyclohexyl 2-cyano-3,3-diphenylacrylate (prepared as in Example 2) |
| 1.50 | 4-tert-butyl-4'-methoxydibenzoylmethane |
| 8.00 | octyl methoxycinnamate |
| 5.00 | zinc oxide |
| 4.00 | castor oil |
| 4.00 | pentaerythritil stearate/caprate/caprylate/adipate |
| 3.00 | glyceryl stearate SE |
| 2.00 | beeswax |
| 2.00 | microcrystalline wax |
| 2.00 | quaternium-18 bentonite |
| 1.50 | PEG-45/dodecyl glycol copolymer |

EXAMPLE 9

Composition for sun blocker containing micropigments

| Mass content (% by weight) | |
|---|---|
| ad 100 | water |
| 10.00 | octyl methoxycinnamate |
| 6.00 | PEG-7 hydrogenated castor oil |
| 6.00 | titanium dioxide, micronized |
| 3.00 | cyclohexyl 2-cyano-3,3-diphenylacrylate (prepared as in Example 2) |
| 1.50 | 4-tert-butyl-4'-methoxydibenzoylmethane |
| 5.00 | mineral oil |
| 5.00 | isoamyl p-methoxycinnamate |
| 5.00 | propylene glycol |
| 3.00 | jojoba oil |
| 3.00 | 4-methylbenzylidenecamphor |
| 2.00 | PEG-45/dodecyl glycol copolymer |
| 1.00 | dimethicone |
| 0.50 | PEG-40 hydrogenated castor oil |
| 0.50 | tocopheryl acetate |
| 0.50 | phenoxyethanol |
| 0.20 | EDTA |

EXAMPLE 10

Non-greasy gel

| Mass content (% by weight) | |
|---|---|
| ad 100 | water |
| 8.00 | octyl methoxycinnamate |
| 7.00 | titanium dioxide, micronized |
| 3.00 | cyclohexyl 2-cyano-3,3-diphenylacrylate (prepared as in Example 2) |
| 1.50 | 4-tert-butyl-4'-methoxydibenzoylmethane |
| 5.00 | glycerol |
| 5.00 | PEG-25 PABA |
| 1.00 | 4-methylbenzylidenecamphor |
| 0.40 | acrylates C10–C30 alkyl acrylate crosspolymer |
| 0.30 | imidazolidinylurea |
| 0.25 | hydroxyethylcellulose |
| 0.25 | sodium methylparaben |
| 0.20 | disodium EDTA |
| 0.15 | fragrance |
| 0.15 | sodium propylparaben |
| 0.10 | sodium hydroxide |

EXAMPLE 11

Suncream (SPF 20)

| Mass content (% by weight) | |
|---|---|
| ad 100 | water |
| 8.00 | octyl methoxycinnamate |
| 8.00 | titanium dioxide, micronized |
| 6.00 | PEG-7 hydrogenated castor oil |
| 3.00 | cyclohexyl 2-cyano-3,3-diphenylacrylate (prepared as in Example 2) |
| 1.50 | 4-tert-butyl-4'-methoxydibenzoylmethane |
| 6.00 | mineral oil |
| 5.00 | zinc oxide |
| 5.00 | isopropyl palmitate |
| 0.30 | imidazolidinylurea |
| 3.00 | jojoba oil |

-continued

| Mass content (% by weight) | |
|---|---|
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | disodium EDTA |
| 0.15 | propylparaben |

EXAMPLE 12

Water-resistant suncream

| Mass content (% by weight) | |
|---|---|
| ad 100 | water |
| 8.00 | octyl methoxycinnamate |
| 5.00 | PEG-7 hydrogenated castor oil |
| 5.00 | propylene glycol |
| 4.00 | isopropyl palmitate |
| 4.00 | caprylic/capric triglyceride |
| 3.00 | cyclohexyl 2-cyano-3,3-diphenylacrylate (prepared as in Example 2) |
| 1.50 | 4-tert-butyl-4'-methoxydibenzoylmethane |
| 4.00 | glycerol |
| 3.00 | jojoba oil |
| 2.00 | 4-methylbenzylidenecamphor |
| 2.00 | titanium dioxide, micronized |
| 1.50 | PEG-45/dodecyl glycol copolymer |
| 1.50 | dimethicone |
| 0.70 | magnesium sulfate |
| 0.50 | magnesium stearate |
| 0.15 | fragrance |

EXAMPLE 13

Sunmilk (SPF 6)

| Mass content (% by weight) | |
|---|---|
| ad 100 | water |
| 10.00 | mineral oil |
| 6.00 | PEG-7 hydrogenated castor oil |
| 5.00 | isopropyl palmitate |
| 3.50 | octyl methoxycinnamate |
| 3.00 | cyclohexyl 2-cyano-3,3-diphenylacrylate (prepared as in Example 2) |
| 1.50 | 4-tert-butyl-4'-methoxydibenzoylmethane |
| 3.00 | caprylic/capric triglyceride |
| 3.00 | jojoba oil |
| 2.00 | PEG-45/dodecyl glycol copolymer |
| 0.70 | magnesium sulfate |
| 0.60 | magnesium stearate |
| 0.50 | tocopheryl acetate |
| 3.00 | glycerol |
| 0.25 | methylparaben |
| 0.15 | propylparaben |
| 0.05 | tocopherol |

EXAMPLE 14

Day lotion with UV protection

| Mass content (% by weight) | |
|---|---|
| ad 100 | water |
| 2.00 | cetearyl alcohol |
| 1.00 | glycerol monostearate |
| 2.00 | vaseline |
| 7.50 | octyl methoxycinnamate |
| 4.00 | octyl salicylate |
| 3.00 | cyclohexyl 2-cyano-3,3-diphenylacrylate (prepared as in Example 2) |
| 1.50 | 4-tert-butyl-4'-methoxydibenzoylmethane |
| 0.50 | dimethicone |
| 5.00 | propylene glycol |
| 0.20 | EDTA |
| 0.20 | carbomer |
| 5.00 | $C_{12}$–$C_{15}$-alkyl benzoate |
| 0.27 | triethanolamine |
| 1.00 | tocopheryl acetate |
| q.s. | fragrance |

EXAMPLE 15

Daycream with UV protection

| Mass content (% by weight) | |
|---|---|
| ad 100 | water |
| 2.00 | cetearyl alcohol |
| 2.00 | cetyl alcohol |
| 1.00 | glycerol monostearate |
| 2.00 | vaseline |
| 7.50 | octyl methoxycinnamate |
| 4.00 | octyl salicylate |
| 3.00 | cyclohexyl 2-cyano-3,3-diphenylacrylate (prepared as in Example 2) |
| 1.50 | 4-tert-butyl-4'-methoxydibenzoylmethane |
| 4.00 | propylene glycol |
| 0.20 | EDTA |
| 0.20 | carbomer |
| 0.20 | xanthan |
| 0.20 | $C_{10}$–$C_{30}$-alkyl acrylate crosspolymer |
| 5.00 | $C_{12}$–$C_{15}$-alkyl benzoate |
| 0.54 | triethanolamine |
| 1.00 | tocopheryl acetate |
| q.s. | fragrance |
| q.s. | preservative |

EXAMPLE 16

Liquid make-up

| Mass content (% by weight) | |
|---|---|
| ad 100 | water |
| 2.00 | cetearyl alcohol |
| 2.00 | ceteareth 25 |
| 6.00 | glycerol monostearate |
| 1.00 | cetyl alcohol |
| 8.00 | paraffin oil |
| 7.00 | cetearyl octanoate |
| 0.2 | dimethicone |
| 3.00 | propylene glycol |
| 1.00 | panthenol |

-continued

| | Mass content (% by weight) |
|---|---|
| 3.00 | cyclohexyl 2-cyano-3,3-diphenylacrylate (prepared as in Example 2) |
| 1.50 | 4-tert-butyl-4'-methoxydibenzoylmethane |
| 3.50 | octyl methoxycinnamate |
| 0.1 | bisabolol |
| 5.70 | titanium dioxide |
| 1.10 | iron oxide |
| q.s. | fragrance |

EXAMPLE 17

Hair gel with sun protection

| | Mass content (% by weight) |
|---|---|
| ad 100 | water |
| 1.20 | carbomer |
| 0.50 | hydroxyethylcellulose |
| 4.00 | triethanolamine |
| 0.70 | PEG-40 hydrogenated castor oil |
| 1.50 | cyclohexyl 2-cyano-3,3-diphenylacrylate (prepared as in Example 2) |
| 0.70 | 4-tert-butyl-4'-methoxydibenzoylmethane |
| 2.80 | octyl methoxycinnamate |
| 5.00 | propylene glycol |
| 0.01 | EDTA |
| q.s. | fragrance |
| q.s. | Sicovit Patent Blue 85 E 131 |

EXAMPLE 18

Standardized method for determining photostability (sun test)

A 2% strength by weight alcoholic solution of the light protection agent to be tested was applied, using an Eppendorf pipette (20 μl), to the milled area of a small glass plate. Owing to the presence of the alcohol, the solution distributed uniformly on the roughened surface of the glass. (The amount applied corresponds to the amount of light protection agent required to achieve an average sun protection factor in suncreams.) In the test, 4 small glass plates were irradiated in each case. The irradiation time was 30/60/90/120 minutes in each case. The small glass plates were cooled slightly during irradiation by water cooling located at the base of the suntest apparatus. The temperature inside the sun test apparatus was 40° C. during irradiation. After the samples had been irradiated, they were washed with ethanol in a dark 50 ml graduated flask, and measured using a photometer. The blank samples were likewise applied to small glass plates and evaporated for 30 minutes at room temperature. Like the other samples, they were washed off with ethanol, diluted to 100 ml and measured.

| Stabilizer | Photostability of Parsol 1798*) without stabilizer | Photostability of Parsol 1789 containing 1% of stabilizer | Photostability of Parsol 1789 containing 2% of stabilizer |
|---|---|---|---|
| Compound from Example 1 | 30 min**): 64% 60 min: 28% 90 min: 12% | 30 min: 92% 60 min: 81% 90 min: 69% | 30 min: 94% 60 min: 90% 90 min: 85% |
| Compound from Example 2 | 30 min: 64% 60 min: 28% 90 min: 12% | 30 min: 95% 60 min: 81% 90 min: 73% | 30 min: 94% 60 min: 89% 90 min: 85% |
| Compound from Example 3 | 30 min: 64% 60 min: 28% 90 min: 12% | 30 min: 87% 60 min: 80% 90 min: 65% | 30 min: 96% 60 min: 85% 90 min: 81% |

*) 4-(1,1-Dimethylethyl)-4'-methoxydibenzoylmethane
**) Irradiation time

We claim:

1. A cosmetic or dermatological preparation comprising
a) 0.1 to 10% by weight of one or more 3,3-diphenylacrylates of the formula I,

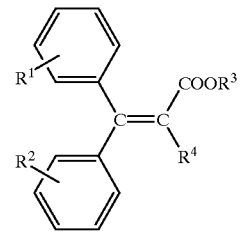

in which the substituents independently of one another have the following meanings:
$R^1$ and $R^2$ are hydrogen, $C_1$–$C_{12}$-alkyl, $C_1$–$C_{12}$-alkoxy;
$R^3$ is $C_3$–$C_{10}$-cycloalkyl, optionally substituted;
$R^4$ is hydrogen, CN and b) 0.1 to 10% by weight of one or more dibenzoylmethane derivatives of the formula II,

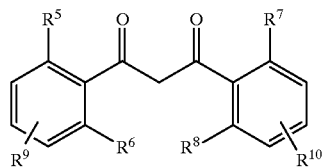

in which the substituents independently of one another have the following meanings:
$R^5$ to $R_8$ are hydrogen, $C_1$–$C_4$-alkyl;
$R^9$ and $R^{10}$ are hydrogen, $C_1$–$C_{12}$-alkyl, $C_1$–$C_{12}$-alkoxy.

2. A cosmetic or dermatological preparation as claimed in claim 1, comprising
a) 0.1 to 10% by weight of one or more 3,3-diphenylacrylates of the formula Ib,

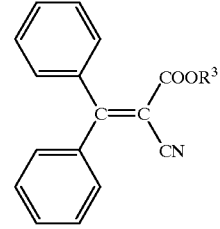

in which $R^3$ is $C_5$–$C_8$-cycloalkyl, optionally substituted, and b) 0.1 to 10% by weight of one or more dibenzoylmethane derivatives, chosen from the group consisting of 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane.

3. A cosmetic or dermatological preparation as claimed in either of claims 1, comprising
   a) 0.1 to 10% by weight of one or more 3,3-diphenylacrylates of the formula Ib,

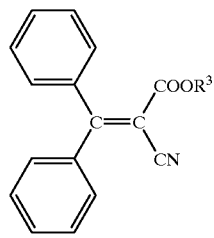

Ib in which $R^3$ is $C_5$–$C_8$-cycloalkyl, optionally substituted, and
   b) 0.1 to 10% by weight of 4-tert-butyl-4'-methoxydibenzoylmethane.

4. A cosmetic or dermatological preparation as claimed in any of claims 1, comprising 0.1 to 6% by weight of component a).

5. A cosmetic or dermatological preparation as claimed in any of claims 1, comprising 1.5 to 2.5% by weight of component a).

6. A cosmetic or dermatological preparation as claimed in any of claims 1, comprising 0.2 to 7% by weight of component b).

7. A cosmetic or dermatological preparation as claimed in any of claims 1, comprising 0.4 to 5% by weight of component b).

8. A cosmetic or dermatological preparation as claimed in claim 1, comprising components a) and b) in a molar ratio a:b of 0.5:1 to 10:1.

9. A cosmetic or dermatological preparation as claimed in claim 1, comprising components a) and b) in a molar ratio a:b of 1:1 to 8:1.

10. A cosmetic or dermatological preparation as claimed in any of claims 1, having a sun protection factor of >10.

11. A method for the protection of human skin or human hair against solar rays, which comprises application of cosmetic or dermatological preparations, defined as in claim 1, to the human skin or human hair to be protected, alone or together with compounds which absorb in the UV region and are known per se for cosmetic or dermatological preparations.

* * * * *